US009517003B2

(12) United States Patent
Lee (10) Patent No.: US 9,517,003 B2
(45) Date of Patent: Dec. 13, 2016

(54) INSERTABLE LIGHTING DEVICE

(71) Applicant: Meng-G Martin Lee, Gibsonia, PA (US)

(72) Inventor: Meng-G Martin Lee, Gibsonia, PA (US)

(*) Notice: Subject to any disclaimer, the term of this patent is extended or adjusted under 35 U.S.C. 154(b) by 382 days.

(21) Appl. No.: 14/287,306

(22) Filed: May 27, 2014

(65) Prior Publication Data

US 2015/0025325 A1    Jan. 22, 2015

Related U.S. Application Data

(60) Provisional application No. 61/856,328, filed on Jul. 19, 2013.

(51) Int. Cl.
  *A61B 1/06* (2006.01)
  *A61B 1/07* (2006.01)
(52) U.S. Cl.
  CPC .............. *A61B 1/07* (2013.01); *A61B 90/30* (2016.02); *A61B 2090/306* (2016.02)
(58) Field of Classification Search
  CPC . A61B 90/30; A61B 2090/306; A61B 1/3132; A61B 17/3478; A61B 1/07
  USPC ................................................ 606/185, 249
  See application file for complete search history.

(56) References Cited

U.S. PATENT DOCUMENTS

| 5,165,773 | A | 11/1992 | Nath |
| 5,910,816 | A | 6/1999 | Fontenot et al. |
| 6,030,364 | A | 2/2000 | Durgin et al. |
| 6,963,688 | B2 | 11/2005 | Nath |
| 8,398,240 | B2 | 3/2013 | Smith |
| 8,485,972 | B2 | 7/2013 | Papac et al. |
| 8,512,232 | B2 | 8/2013 | Rothberg et al. |
| 2005/0171408 | A1* | 8/2005 | Parker ............... A61B 17/02 600/249 |
| 2008/0177295 | A1* | 7/2008 | Vitali .............. A61B 17/3417 606/185 |
| 2009/0192390 | A1 | 7/2009 | Berguer et al. |
| 2009/0240111 | A1 | 9/2009 | Kessler et al. |
| 2014/0100431 | A1* | 4/2014 | Curcillo ........... A61B 17/3421 600/249 |

\* cited by examiner

*Primary Examiner* — Si Ming Ku
(74) *Attorney, Agent, or Firm* — The Webb Law Firm (57) ABSTRACT

The present invention relates to an insertable lighting device that includes an optical fiber assembly 40 that resides slidably within the elongated interior cavity 58 of an introducer sheath 10 that includes an incision blade 12 on the first (or forward) end 49 thereof, which can be inserted through a cavity wall 32 and into an internal cavity 97. The introducer sheath 10 is also slidably positionable over and along the optical fiber assembly 40. The insertable lighting device also includes a light source assembly 22 which includes a light source 20 that introduces light into the optical fiber 18 of the optical fiber assembly 40. The first optical fiber assembly end 43 is adapted to emit light therefrom. The present invention also relates to a method of illuminating an internal cavity with the insertable lighting device.

16 Claims, 4 Drawing Sheets

INSERTABLE LIGHTING DEVICE

CROSS REFERENCE TO RELATED APPLICATION

This application is entitled to and claims priority to U.S. Patent Application No. 61/856,328, filed on Jul. 19, 2013, the disclosure of which is incorporated herein by reference in its entirety.

FIELD

The present invention relates to insertable lighting devices that include an optical fiber assembly that resides slidably within the elongated interior cavity of an introducer sheath that includes an incision blade on the first end thereof, which can be inserted into a cavity, and to methods of illuminating an internal cavity with such insertable lighting devices.

BACKGROUND

Procedures performed within an intra-cavity space, such as but not limited to surgical and/or diagnostic procedures, typically involve inserting a device that includes one or more instruments, such as clamps, blades, and/or scissors, into a cavity, such as an abdominal cavity. The instruments introduced into the cavity are typically manipulated directly or indirectly by an operator, such as a surgeon, from outside of the cavity. To ensure proper manipulation of the inserted instruments, illumination of at least a portion of the cavity is required. The inserted device generally includes an integral light source through-which and/or around-which the instruments are positioned. Such integral light sources can be problematic under some circumstances, such as when one or more of the instruments undesirably obstruct a portion of the light emanating from the integral light source. In some instances, the integral light source is capable of illuminating only an area forward of the insertable device, rather than a broader area.

It would be desirable to develop insertable lighting devices that can be inserted separately from insertable devices that include one or more instruments. It would be further desirable that such newly developed insertable lighting devices be capable of illuminating a broad area or a plurality of areas within the cavity.

SUMMARY

In accordance with the present invention, there is provided an insertable lighting device comprising, (a) an optical fiber assembly that comprises, (i) an optical fiber that is encased at least partially within (ii) a pliable sheath, wherein the optical fiber assembly is flexible, and has a first optical fiber assembly end that is adapted to emit light, a second optical fiber assembly end, and a first length, in which the first optical fiber assembly end faces a forward direction. The insertable lighting device further comprises, (b) an introducer sheath having a second length that is less than said first length, which comprises: (i) a first introducer sheath end that comprises an incision blade; (ii) a second introducer sheath end; and (iii) an elongated interior cavity, wherein the optical fiber assembly resides slidably (or slidingly) within the elongated interior cavity of the introducer sheath, the introducer sheath is slidably (or slidingly) positionable over and along the optical fiber assembly, and the first introducer sheath end faces the forward direction. The insertable lighting device further comprises, (c) a light source assembly attached to the second optical fiber assembly end, in which the light source assembly comprises a light source that introduces light into the optical fiber.

In accordance with the present invention, there is further provided a method of illuminating an internal cavity (or intra-cavity space) comprising: (A) providing an insertable lighting device as described above: (B) positioning (i) the introducer sheath, and/or (ii) the optical fiber assembly, such that, the incision blade of the introducer sheath is positioned forward of the first optical fiber assembly end; (C) inserting the incision blade and a portion of the introducer sheath through a cavity wall into the internal cavity (or intra-cavity space); (D) positioning (i) the introducer sheath, and/or (ii) the optical fiber assembly, such that the first optical fiber assembly end is positioned forward beyond the incision blade and within the internal cavity; and (E) illuminating at least a portion of the internal cavity with light emanating from the first optical fiber assembly end.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWINGS

In FIGS. 1-5 like characters refer to the same components unless otherwise stated.

DETAILED DESCRIPTION

As used herein, the articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

Unless otherwise indicated, all numbers expressing, quantities, dimensions and so forth used in the specification and claims are to be understood as modified in all instances by the term "about."

As used herein, spatial or directional terms, such as "left", "right", "inner", "outer", "above", "below", and the like, relate to the invention as it is depicted in the drawing figures. It is to be understood, however, that the invention can assume various alternative orientations and, accordingly, such terms are not to be considered as limiting.

As used herein, the term "polymer" means homopolymers (e.g., prepared from a single monomer species), copolymers (e.g., prepared from at least two monomer species), and graft polymers.

All documents, such as but not limited to issued patents and patent applications, referred to herein, and unless otherwise indicated, are to be considered to be "incorporated by reference" in their entirety.

Figure 1:
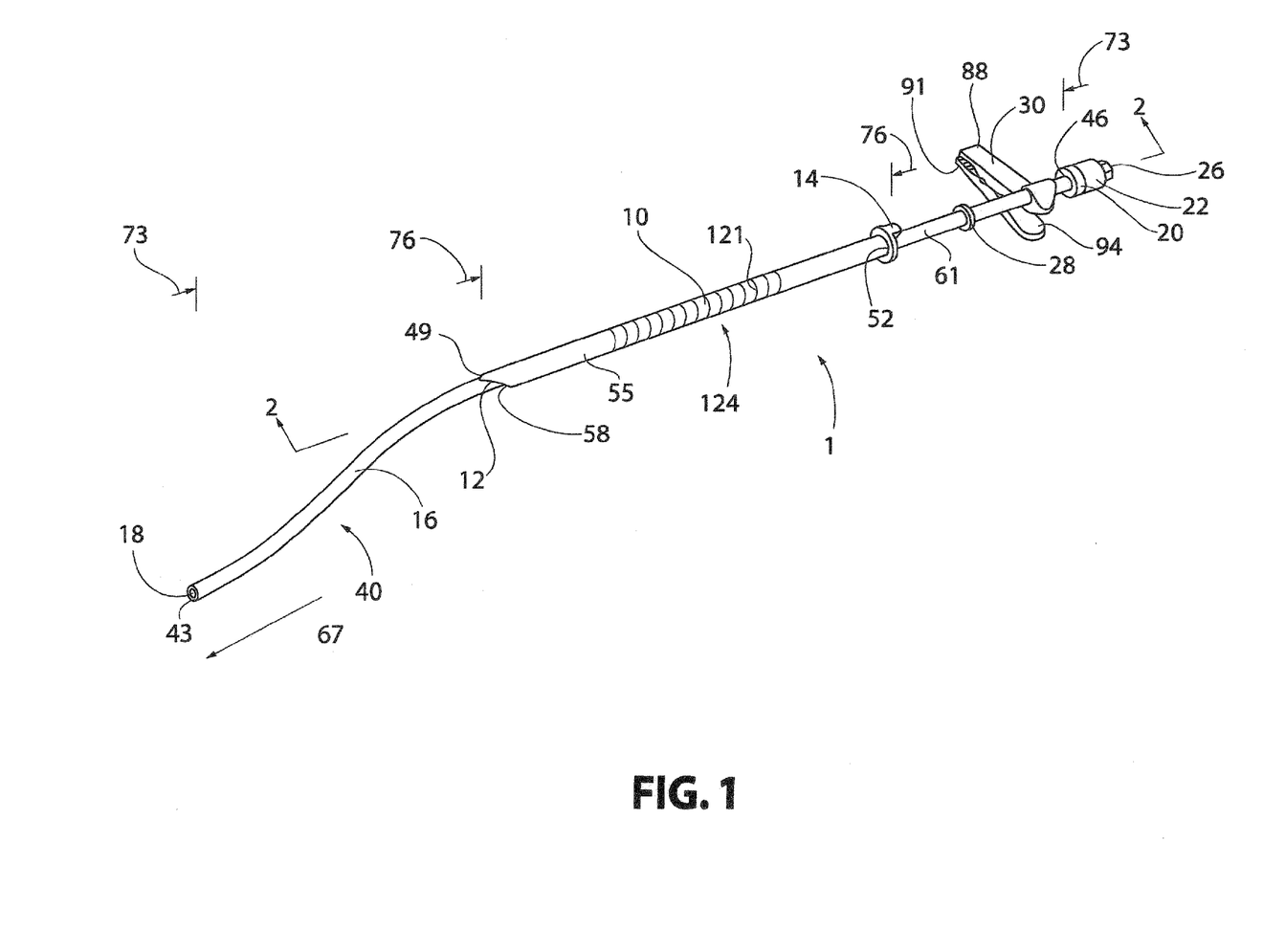
FIG. 1 is a representative perspective view of an insertable lighting device according to some embodiments of the present invention.
Figure 2:
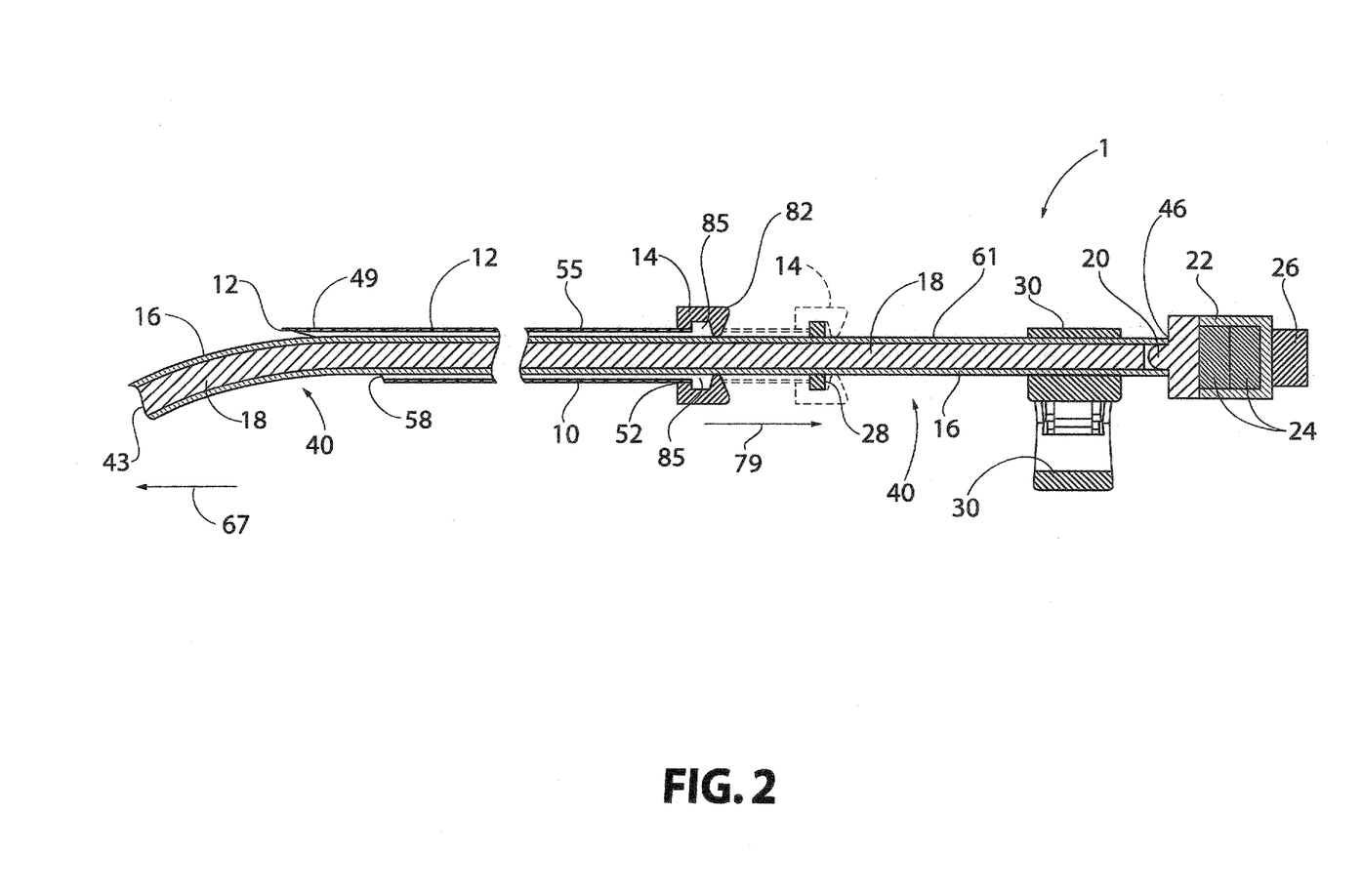
FIG. 2 is a representative sectional side elevational view along line 2-2 of the insertable lighting device of FIG. 1.

With reference to FIG. 1 and FIG. 2 of the drawings and in accordance with some embodiments of the present invention, insertable lighting device 1 includes an optical fiber assembly 40. Optical fiber assembly 40, with some embodiments, includes an optical fiber 18 that is encased at least partially within a pliable sheath 16. The optical fiber of the optical fiber assembly can, with some embodiments, be composed of a single optical fiber (as depicted in the drawings) or a plurality of optical fibers (not depicted). The optical fiber can be fabricated from any suitable art-recognized material or combination of materials, such as: one or more glass materials, such as inorganic glasses, such as silicate based glass; organic polymers, such as thermoplastic and/or thermoset polymeric materials, such as polyacrylates, polyalkylmethacrylates, such as polymethylmethacrylates, polyethylmethacrylates, polypropylmethacrylates, and the like, and polycarbonates; and combinations thereof. With some embodiments, the optical fiber is free of tints. With some further embodiments, the optical fiber includes one or more tints, and the light emitted from the optical fiber is tinted light.

The optical fiber can have any suitable cross-sectional shape or shapes, such as selected from circular shapes, elliptical shapes, polygonal shapes (e.g., triangular, rectangular, pentagonal, hexagonal, heptagonal, octagonal, etc.), irregular shapes, and combinations of two or more such shapes. In accordance with some embodiments, the optical fiber of the optical fiber assembly has a substantially circular cross-sectional shape and a diameter of from 1 mm to 30 mm, or from 1 mm to 20 mm, of 2 mm to 10 mm, inclusive of the recited values.

The optical fiber 18, of optical fiber assembly 40, is at least partially encased in a pliable sheath 16. With some embodiments, the elongated sides of the optical fiber are at least partially encased in a pliable sheath, while the first and second ends of the optical fiber (which correspond to the first optical fiber assembly end 43 and the second optical fiber assembly end 46) are free of the pliable sheath. As used herein, the term "pliable" with regard to the pliable sheath, of the optical fiber assembly, means readily bendable, such that the pliable sheath is readily bendable. With some embodiments, the pliable sheath, and correspondingly the optical fiber assembly, is capable of being bent and after being bent maintains the configuration into which it has been bent. The pliable sheath can, with some embodiments, be fabricated from any suitable art-recognized material, such as, but not limited to, thermoplastic and/or thermoset polymers, such as, urethane polymer, (meth)acrylic polymer, fluoropolymer, polytetrafluoroethylene, polyetheretherketone, polystyrene, cross-linked polystyrene, polyester, polycarbonate, polyolefin, such as polyethylene, polypropylene, and copolymers of ethylene and propylene, acrylonitrile-butadiene-styrene, nylons, such as nylon 6,6, and combinations of two or more thereof.

The pliable sheath of the optical fiber assembly can have any suitable thickness. With some embodiments, the pliable sheath has a thickness of from 1 mm to 15 mm, or from 1 mm to 10 mm, or from 1 mm to 5 mm.

The optical fiber assembly, with some embodiments, is flexible, and has a first optical fiber assembly end 43 that is adapted to emit light, a second optical fiber assembly end 46, and a first length 73 (such as a first linear length 73). The first optical fiber assembly end 43 faces a forward direction as indicated by arrow 67. In accordance with some embodiments, the second optical fiber assembly end 46 is adapted to receive light, such as light from light source assembly 22, as described in further detail herein.

The first length 73 of the optical fiber assembly 40 extends, with some embodiments, from first optical fiber assembly end 43 to second optical fiber assembly end 46. The first length of the optical fiber assembly, with some embodiments, is from 10 cm to 200 cm, or from 15 cm to 100 cm, or from 20 cm to 50 cm.

The first optical fiber assembly end 43 and/or the second optical fiber assembly end 46 can each independently include one or more optical lenses and/or optical filters (not shown), with some embodiments. The optical lenses can, with some embodiments, each independently narrow or broaden the focus of the light introduced into the second optical fiber assembly end 46 and/or of the light that is emitted from the first optical fiber assembly end 43. The optical lenses can each be independently attached to the first (43) and/or second (46) optical fiber assembly ends by methods including, but not limited to: one or more adhesives; and/or unitarily formed as part of, such as machined into, the first (43) and/or second (46) optical fiber assembly ends. The optical filters can, with some embodiments, limit the wavelength(s) or range of wavelengths of the light introduced into and/or emitted from the optical fiber assembly.

The insertable lighting device includes an introducer sheath 10 having a second length 76 (such as a second linear length 76). The second length 76 of the introducer sheath 10 extends from the first introducer sheath end 49 to the second introducer sheath end 52, with some embodiments. The second length 76 of the introducer sheath 10 is less than the first length 73 of the optical fiber assembly 40. The second length of the introducer sheath, with some embodiments, is from 5 cm to 175 cm, or from 10 cm to 90 cm, or from 10 cm to 40 cm.

The introducer sheath 10 further includes: a first introducer sheath end 49 that includes an incision blade 12; a second introducer sheath end 52; and an elongated interior cavity 58. The optical fiber assembly 40 resides slidably (or slidingly) within the elongated interior cavity 58 of the introducer sheath 10. Correspondingly and concurrently, with some embodiments, the introducer sheath 10 is slidably (or slidingly) positionable over and along the optical fiber assembly 40. Correspondingly and concurrently, with some embodiments, the optical fiber assembly 40 is slidably positionable within and along the elongated interior cavity 58 of the introducer sheath 10.

The first introducer sheath end 49 faces the forward direction 67. As such, and in accordance with some embodiments, the first optical fiber assembly end 43 and the first introducer sheath end 49 (including incision blade 12) are oriented in (or towards) the same direction and both face the forward direction 67.

The incision blade 12 can, with some embodiments, be a substantially integral part of the introducer sheath 10, in which case incision blade 12 and introducer sheath 10 together form a substantially unitary structure (as depicted in the drawings). With some further embodiments, the incision blade is a separate structure that is attached to the first introducer sheath end of the introducer sheath (not depicted in the drawings). The incision blade can, with some embodiments, be attached to the first introducer sheath end by attachment systems selected from, but not limited to, adhesives, fasteners, such as rivets and/or screws, and combinations thereof.

The introducer sheath, with some embodiments, is more rigid relative to the optical fiber assembly, which is flexible. The introducer sheath can be fabricated from any suitable art-recognized material or materials, such as, but not limited to, organic polymers, metals, metal alloys, and combinations of two or more thereof. Examples of organic polymers from which the introducer sheath can be fabricated, include, but are not limited to, urethane polymer, (meth)acrylic polymer, fluoropolymer, polybenzamidazole, polyimide, polytetrafluoroethylene, polyetheretherketone, polyamide-imide, polystyrene, cross-linked polystyrene, polyester, polycarbonate, polyolefin, such as polyethylene, polypropylene, and copolymers of ethylene and propylene, acrylonitrile-butadiene-styrene, nylon, such as nylon 6,6,rigid vinyl, and combinations of two or more thereof. Examples of metals from which the introducer sheath can be fabricated with some embodiments include, but are not limited to: ferrous metals, such as stainless steel; copper; aluminum; titanium; and combinations of two or more thereof.

The insertable lighting device further includes, with some embodiments, a light source assembly 22. The light source assembly 22 is attached to the second optical fiber assembly end 46. The light source assembly 22 includes at least one light source 20 that introduces light in the optical fiber 18. Light introduced from light source 20 into the optical fiber 18, such as into second optical fiber assembly end 46, passes through the length of the optical fiber 18, and is emitted from the first optical fiber assembly end 43, with some embodiments. At least some of the light introduced into the second optical fiber assembly end 46 is internally reflected within optical fiber 18, such that a substantial portion (such as at least 95 percent or at least 98 percent) of the light introduced into optical fiber assembly from light source assembly 22, is emitted from the first optical fiber assembly end 43, with some embodiments. The light source can be selected from art-recognized light sources, such as, but not limited to, incandescent lights, halogen lights, light emitting diodes, organic light emitting diodes, and combinations of two or more thereof. The light source assembly can include one or more light filters (not shown) (i) as an integral portion of the light source and/or (ii) positioned between the light source and the second optical fiber assembly end, with some embodiments. The light filter(s) limits the wavelength(s) or range of wavelengths of light that are introduced into the optical fiber from the light source of the light source assembly, with some embodiments. With some additional embodiments, the light filter is an adjustable light filter, which can be adjusted to change the wavelength or range of wavelengths of light that are introduced into the optical fiber from the light source of the light source assembly.

The second introducer sheath end of the insertable lighting device, in accordance with some embodiments, includes a ring extending outwardly from an exterior surface of the introducer sheath, and the insertable lighting device further includes, a ring stop extending outwardly from an exterior surface of the pliable sheath, the ring stop is positioned between the second optical fiber assembly end and the second introducer sheath end. The ring stop and the ring of the introducer sheath are each dimensioned to engage abuttingly with each other, with some embodiments. The abutting engagement of the ring stop and the ring serves, with some embodiments, to provide or define a terminal position that the introducer sheath can be moved back (such as indicated by arrow 79 in FIG. 2) along the optical fiber assembly. Alternatively or additionally, the abutting engagement of the ring stop and the ring serves, with some embodiments, to provide or define a terminal forward position that the first optical fiber assembly end 43 can be positioned forward relative to the first introducer sheath end 49. Alternatively or additionally, the abutting engagement of the ring stop and the ring serves, with some embodiments, to provide or define a maximum distance between the first optical fiber assembly end 43 and the first introducer sheath end 49, when the first optical fiber assembly end 43 is positioned forward relative to the first introducer sheath end 49.

With further reference to FIG. 1 and FIG. 2, the second introducer sheath end 52 of the insertable lighting device 1, in accordance with some embodiments, includes a ring 14 that extends outwardly from an exterior surface 55 of the introducer sheath 10. Ring 14 can extend outward from exterior surface 55 at any suitable angle, such as at an angle of from greater than 0° to 90° relative to exterior surface 55. With some embodiments, ring 14 extends substantially laterally outward from exterior surface 55 of introducer sheath 10, and forms a 90° angle relative to exterior surface 55.

The insertable lighting device 1 further includes, with some embodiments, a ring stop 28 that extends outwardly from an exterior surface 61 of the pliable sheath 16 (of the optical fiber assembly 40). The ring stop 28 is positioned between the second optical fiber assembly end 46 and the second introducer sheath end 52, with some embodiments. Ring stop 28 can extend outward from exterior surface 61 of pliable sheath 16 at any suitable angle, such as at an angle of from greater than 0° to 90° relative to exterior surface 61. With some embodiments, ring stop 28 extends substantially laterally outward from exterior surface 61 of pliable sheath 16, and forms a 90° angle relative to exterior surface 61. Ring stop 28 is positioned between the second optical fiber assembly end 46 and the second introducer sheath end 52, with some embodiments.

Ring stop 28 and ring 14 of introducer sheath 10 are each dimensioned to engage abuttingly with each other. Ring stop 28 and ring 14 can each independently have any suitable shape selected from, but not limited to, circular shapes, elliptical shapes, polygonal shapes (e.g., triangular, rectangular, pentagonal, hexagonal, heptagonal, octagonal, etc.), irregular shapes, and combinations of two or more such shapes. Ring stop 28 and ring 14 can be held (or maintained) in abutting relationship by systems including, but not limited, one or more clamps (not shown), a contact adhesive (not shown), and combinations thereof.

The ring and the ring stop are each adapted to engage snap-fittingly with each other, in accordance with some embodiments. Any suitable art-recognized snap-fitting system or systems can be used with the ring and the ring stop. With some embodiments: one or more prongs extend outward from ring 14 (and laterally along or relative to optical fiber assembly 40 towards ring stop 28), which engage snap fittingly with recesses and/or apertures in ring stop 28; and/or one or more prongs extend outward from ring stop 28 (and laterally along or relative to optical fiber assembly 40 towards ring 14), which engage snap fittingly with recesses and/or apertures in ring 14 (in each case not shown).

With further reference to FIGS. 1 and 2, and in accordance with some embodiments, ring 14 includes at least one flexible extension 82, that extends laterally along or relative to optical fiber assembly 40 towards ring stop 28, and which defines one or more chambers 85 within ring 14. Ring stop 28 and each chamber 85 are each dimensioned such that ring stop 28 is reversibly received within each chamber 85, when ring 14 and ring stop 28 are brought into snap-fitting engagement. As depicted in FIG. 2, ring 14 includes two flexible extensions 82 that each define a chamber 85. See, for example, the dashed line representations in FIG. 2. For purposes of non-limiting illustration, and with reference to FIG. 2, when introducer sheath 10 is moved back along (or relative to) optical fiber assembly 40, as indicated by arrow 79, each flexible extension 82 of ring 14 extends out and around ring 14, and ring 14 is reversibly and snap-fittingly received within each chamber 85. Subsequently (i) moving the introducer sheath in a forward direction (such as indicated by arrow 67), and/or (ii) moving the optical fiber assembly 40 in a rearward direction (such as indicated by arrow 79), results in ring stop 28 being removed from chamber 85, and thereby correspondingly reversing the snap-fitting engagement of ring 14 and ring stop 28, with some embodiments.

In accordance with some embodiments of the present invention, at least a portion of an exterior surface of the introducer sheath is defined by (or includes) a plurality of ribs. The ribs, with some embodiments, are outwardly extending ribs, and each pair of adjacent ribs is separated by a depression (or recess) therebetween. The plurality of ribs, with some embodiments, serve to retain the introducer sheath in place relative to a cavity wall through which the incision blade and a portion of the introducer sheath has been inserted. With some embodiments, the plurality of ribs and the cavity wall engage frictionally and/or intermeshingly together. While not intending to be bound by any theory, it is believed that portions of the cavity wall material surrounding the introducer sheath extend into the depressions (or recesses) between adjacent ribs, and correspondingly the ribs extend into the cavity wall material therearound, which serves to retain the introducer sheath in place relative to the portion of the cavity wall through-which it has been inserted. The plurality of ribs can, with some embodiments, have any suitable orientation or combination of orientations relative to each other, such as between each pair of adjacent ribs. The plurality of ribs, with some embodiments, can be substantially parallel to each other, and/or can together form one or more helical (or screw-like) patterns. With some embodiments, the whole of the exterior surface of the introducer sheath is defined by a plurality of ribs. With some further embodiments, less than the whole (but some) of the exterior surface of the introducer sheath is defined by a plurality of ribs. With some additional embodiments, a middle portion of the exterior surface of the introducer sheath is defined by a plurality of ribs. In accordance with some further embodiments, the incision blade of the introducer sheath is free of the plurality of ribs.

For purposes of non-limiting illustration, and with reference to FIG. 1, a portion of exterior surface 55 of introducer sheath 10 is defined by a plurality of ribs 121 (which are not shown in FIGS. 2-5). With some embodiments, and as depicted in FIG. 1, a middle portion 124 of exterior surface 55 of introducer sheath 10 is defined by a plurality of ribs 121.

The light source of the light source assembly of the insertable lighting device of the present invention can be electrically powered by an internal power source (such as one or more internal batteries and/or an internal fuel cell) and/or an external power source (such as an external battery, an external fuel cell, and/or an electricity grid). The light source assembly of the insertable lighting device of the present invention, with some embodiments, further includes: a power source; and a power adjuster. With reference to FIG. 1 and FIG. 2, and in accordance with some embodiments, light source assembly 22 further includes a power source 24, and a power adjuster 26.

Power source 24, as depicted, is an internal power source and, with some embodiments, includes at least one battery. The batteries of power source 24 can be selected from art-recognized batteries, such as, but not limited to, primary batteries, such as alkaline batteries, and/or secondary batteries (or rechargeable batteries), such as lithium ion batteries. With some embodiments the power source 24 of the light source assembly is a fuel cell. The power source 24 and the light source 20 are electrically connected, with some embodiments, by appropriate electrical connections (not shown).

The power adjuster 26 is an electrical power adjuster with some embodiments, and adjusts the amount of electricity, or electrical power, that is transferred from the power source 24 to the light source 20, and correspondingly the amount of light, such as lumens, that is emitted from light source 20. The power adjuster, with some embodiments, provides a variable (or gradient) adjustment of power between an off-setting (or zero power setting) and a predetermined maximum-setting. The power adjuster, with some further embodiments, acts as an on-off switch, having an off-setting (or zero power setting) and a predetermined maximum-setting, without any variable power adjustment there-between. Power adjuster 26 is electrically connected to power source 24 and optionally light source 20 by appropriate electrical connections (not shown).

The light introduced into the optical fiber of the optical fiber assembly from the light source, with some embodiments, includes visible light and/or non-visible light, which can in each case be independently coherent or non-coherent. With some embodiments, the light, introduced into the optical fiber by the light source, is selected from visible light, infrared light, ultraviolet light, and combinations of two or more thereof. The visible light introduced into the optical fiber, with some embodiments, includes one or more wavelengths from 380 nm to 700 nm. The ultraviolet light introduced into the optical fiber, with some embodiments, includes one or more wavelengths that are less than the lower limit of visible light, such as from 100 nm to less than 380 nm. Infrared light introduced into the optical fiber, with some embodiments, includes one or more wavelengths that are greater than the upper limit of visible light, such as from greater than 700 nm to 1 mm.

The light emitted from the first optical fiber assembly end, with some embodiments, corresponds substantially to the light that is introduced into the second optical fiber assembly end by the light source, as described above. The light emitted from the first optical fiber assembly end, with some embodiments, includes visible light and/or non-visible light, which in each case can be independently coherent or non-coherent. With some embodiments, the light emitted from the first optical fiber assembly end, is selected from visible light, infrared light, ultraviolet light, and combinations of two or more thereof.

The visible light introduced into the optical fiber, and correspondingly the light emitted from the first optical fiber assembly end can, in each case independently have any suitable color, such as white light, red light, green light, and blue light.

The light introduced into the optical fiber (and in particular into the second optical fiber assembly end) by the light source includes substantially coherent light (or laser light), with some embodiments. The coherent light can include coherent visible light and/or coherent non-visible light. With some embodiments, the coherent light is selected from coherent visible light, coherent infrared light, coherent ultraviolet light, and combinations of two or more thereof. The coherent visible light can, with some embodiments, have any suitable color, such as coherent red light, coherent green light, or coherent blue light.

The light emitted from the optical fiber (and in particular from the first optical fiber assembly end) includes substantially coherent light (or laser light), with some embodiments. The coherent light emitted from the first optical fiber assembly end includes coherent visible light and/or coherent non-visible light, with some embodiments. With some further embodiments, the coherent light emitted from the first optical fiber assembly end is selected from coherent visible light, coherent infrared light, coherent ultraviolet light, and combinations of two or more thereof. The coherent visible light emitted from the first optical fiber assembly end can, with some embodiments, have any suitable color, such as coherent red light, coherent green light, or coherent blue light.

The insertable lighting device of the present invention further includes, with some embodiments, a retainer that is attached to the exterior surface of the pliable sheath, in which the retainer is positioned between the second introducer sheath end and the second optical fiber assembly end. The retainer serves to hold the insertable lighting device in place during use by being attached to a separate structure, such as a stationary post or rod, with some embodiments. With reference to FIG. 1 and FIG. 2, insertable lighting device 1 includes a retainer 30 that is attached to exterior surface 61 of pliable sheath 16. Retainer 30 is positioned between second introducer sheath end 52 and second optical fiber assembly end 46, with some embodiments. The retainer can be fabricated from any suitable materials, such as one or more metals and/or one or more organic polymers, including those classes and examples as described herein with regard to other components of the insertable lighting devices of the present invention.

The retainer can extend outward from the exterior surface of the pliable sheath of the optical fiber assembly at any suitable angle, such as from greater than 0° to 90°, relative to the exterior surface of the pliable sheath, with some embodiments. In accordance with some further embodiments, the retainer extends substantially laterally outward from the optical fiber assembly, such as forming substantially a 90° angle relative to the exterior surface of the pliable sheath.

The retainer of the insertable lighting device can have any suitable configuration. With some embodiments, the retainer is in the form of a rod that can be reversibly attached to a separate structure by one or more retainers, such as clamps and/or fasteners (not shown in the drawings).

With some embodiments, the retainer is a retainer clip. With reference to FIG. 1, retainer 30 is a retainer clip 30 having a first clip portion 88 and a second clip portion 91 that are resiliently opposed to each other. Second clip portion 91 of retainer clip 30 further includes a tab extension 94. When tab extension 94 is depressed towards optical fiber assembly 40, first clip portion 88 and second clip portion 91 are pivetedly opened and separated relative to each other, allowing a separate structure (not shown) to be interposed and retained there-between when the first and second clip portions (88, 91) are returned to resilient opposition.

The insertable lighting device of the present invention, with some embodiments, includes a ring and ring stop as described previously herein. When including a ring and ring stop as described previously herein, the retainer is positioned such that it is not interposed between the ring and the ring stop. With some embodiments, the insertable lighting device includes a retainer attached to the exterior surface of the pliable sheath, and in which the retainer is positioned between the ring stop and the second optical fiber assembly end. With reference to FIG. 1, and for purposes of non-limiting illustration, retainer 30 is positioned between ring stop 28 and second optical fiber assembly end 46. Correspondingly retainer 30 is not positioned (or interposed) between ring 14 and ring stop 28, with some embodiments.

Figure 3:
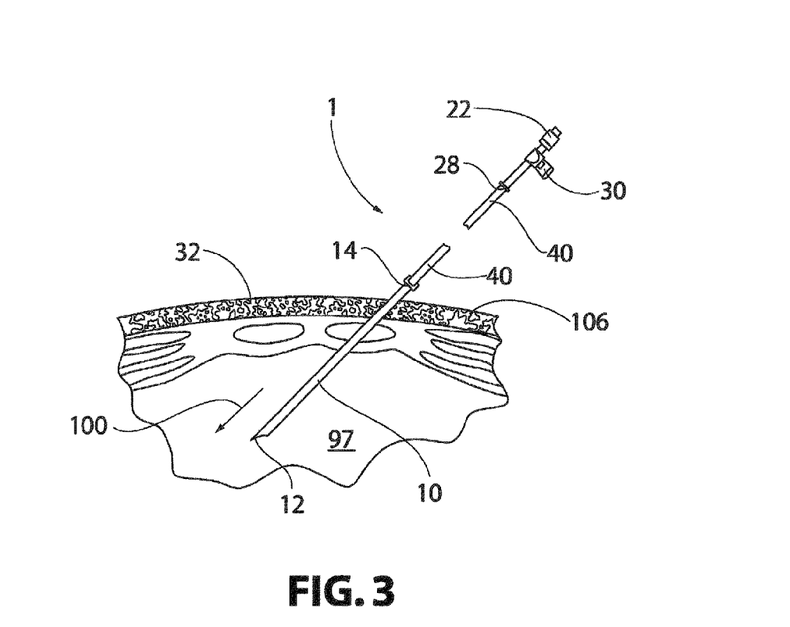
FIG. 3 is a representative partial sectional view of an insertable lighting device according to an embodiment of the present invention, in which the introducer sheath thereof is inserted into a cavity.

The first optical fiber assembly end is dimensioned to be positioned (such as withdrawn) within the elongated interior cavity of the introducer sheath, with some embodiments. With reference to FIG. 1 and FIG. 2, first optical fiber assembly end 43 as depicted is dimensioned such that it can be positioned, such as withdrawn, within elongated interior cavity 58 of introducer sheath 10. With further reference to FIG. 3, first optical fiber assembly end 43 (not visible) of optical fiber assembly 40 is positioned within the elongated interior cavity 58 of introducer sheath 10. Positioning first optical fiber assembly end 43 within the elongated interior cavity 58 of introducer sheath 10, with some embodiments, allows the incision blade 12 of the introducer sheath 10 to be efficiently inserted through a cavity wall and into an underlying internal cavity. With some embodiments, the first optical fiber assembly end and the optical fiber assembly each independently have a largest cross-sectional dimension (such as a diameter) that is less than the diameter (or internal diameter) of the elongated interior cavity of the introducer sheath.

The insertable lighting device of the present invention can be used in or with any suitable application or procedure. With some embodiments, the insertable lighting device of the present invention is used in industrial applications, such as for purposes of illuminating the interior space of a machine or apparatus (such the interior of a pipe) which is defined at least in part by an exterior wall that can be pierced or otherwise penetrated by the incision blade of the introducer sheath.

With some further embodiments, the insertable lighting device of the present invention is used in conjunction with surgical procedures. The insertable lighting device is an insertable internal cavity (or intra-cavity) surgical lighting device, with some embodiments. The insertable internal cavity surgical lighting device of the present invention can be used to illuminate at least the portion of an internal cavity of a living organism, such as, but not limited to an internal cavity of an animal, such as a vertebrate, such as a fish, amphibian, reptile, bird, or mammal, with some embodiments.

The present invention also relates to a method of illuminating an internal cavity (or intra-cavity space), which includes providing the insertable lighting device of the present invention, as described previously herein. With reference to FIGS. 1-5, the method of the present invention further includes positioning (i) the introducer sheath 10, and/or (ii) the optical fiber assembly 40, such that, the incision blade 12 of the introducer sheath 10 is positioned forward of the first optical fiber assembly end 43 of the optical assembly 40, such as depicted in FIG. 3.

With the incision blade 12 of the introducer sheath 10 positioned forward of the first optical fiber assembly end 43, the method of the present invention further includes, inserting the incision blade 12 and a portion of the introducer sheath 10 through a cavity wall 32 into an internal cavity 97. With reference to FIG. 3, the direction of insertion of incision blade 12 through cavity wall 32 is indicated by arrow 100. With some embodiments, the portion of introducer sheath 10 that is introduced into internal cavity 97 extends from first introducer sheath end 49 to no further than ring 14.

With the incision blade 12 and a portion of the introducer sheath 10 inserted through cavity wall 32 and into internal cavity 97, the method of the present invention further includes positioning, (i) the introducer sheath 10, and/or (ii) the optical fiber assembly 40, such that the first optical fiber assembly end 43 is positioned forward beyond the incision blade 12 and within the internal cavity 97. See FIG. 4.

Figure 4:
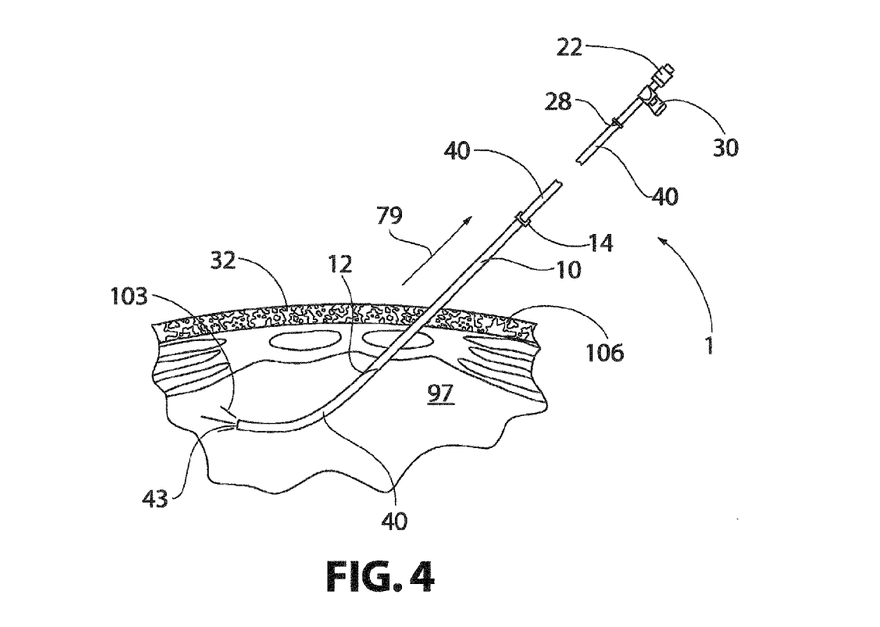
FIG. 4 is a representative partial sectional view of an insertable lighting device according to an embodiment of the present invention, in which the first optical fiber assembly end of the optical fiber assembly is positioned forward beyond the incision blade of the introducer sheath and within a cavity.

With the first optical fiber assembly end 43 positioned forward beyond the incision blade 12 and within the internal cavity 97, the method of the present invention further includes, with some embodiments, illuminating at least a portion of the internal cavity 97 with light 103 emanating from the first optical fiber assembly end 43 of the optical fiber assembly 40.

Figure 5:
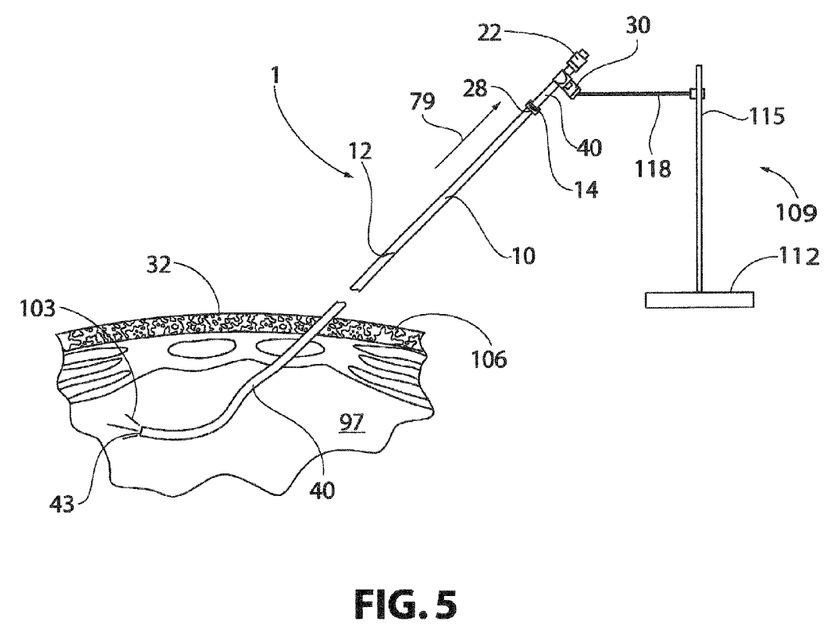
FIG. 5 is a representative partial sectional view of an insertable lighting device according to an embodiment of the present invention, in which the first optical fiber assembly end of the optical fiber assembly is positioned within a cavity, and the introducer sheath is positioned externally of the cavity.

In accordance with some embodiments, the method of the present invention further includes, withdrawing the incision blade and the introducer sheath from the internal cavity, such that the incision blade is positioned externally of an outer surface of the cavity wall, and the first optical fiber assembly end is positioned within the internal cavity. With reference to FIGS. 4 and 5, the incision blade 12 and the introducer sheath 10 are withdrawn from the internal cavity 97, such that the incision blade 12 (and correspondingly the introducer sheath 10) is/are positioned externally of an outer surface 106 of the cavity wall 32, and the first optical fiber assembly end 43 of the optical fiber assembly 40 is positioned within the internal cavity 97.

The insertable lighting device of the present invention further includes a ring and a ring stop, which are each dimensioned to engage abuttingly with each other, as described previously herein. When the insertable lighting device includes a ring and a ring stop, which are each dimensioned to engage abuttingly with each other, as described previously herein, the method of the present invention further includes, with some embodiments, after withdrawing the incision blade and the introducer sheath from the internal cavity, positioning abuttingly together the ring of the introducer sheath and the ring stop. With reference to FIG. 5, after withdrawing the incision blade 12 and the introducer sheath 10 from the internal cavity 97, the ring 14 of the introducer sheath 10 and the ring stop 28 are positioned in abutting relationship with each other.

The ring of the introducer sheath and the ring stop are each adapted to engage snap-fittingly with each other, as described previously herein with regard to some embodiments, in which case the method of the present invention further includes, with some embodiments, positioning the ring of the introducer sheath and the ring stop in snap-fitting engagement with each other. With reference to FIG. 5, after withdrawing the incision blade 12 and the introducer sheath 10 from the internal cavity 97, the ring 14 of the introducer sheath 10 and the ring stop 28 are positioned in snap-fitting engagement with each other. Positioning the ring 14 of the introducer sheath 10 and the ring stop 28 in snap-fitting engagement with each other, after withdrawing the incision blade 12 and the introducer sheath 10 from the internal cavity 97, keeps the incision blade 12 separated from the external surface 106 of the cavity wall 32, so as to avoid unnecessarily contacting or piercing the cavity wall 32 with the incision blade 12, with some embodiments.

The insertable lighting device of the present invention further includes a retainer, such as retainer 30, which is positioned between the ring stop and the second optical fiber assembly end, as described previously herein with regard to some embodiments, in which case the method of the present invention further includes attaching the retainer to an external support, with some embodiments. The external support can be any suitable structure to which the retainer can be secured, for purposes, such as, retaining the insertable lighting device in a particular position relative to the cavity wall and/or the first optical assembly end 43 in a particular position within internal cavity 97, with some embodiments. With reference to FIGS. 1, 2, and 5, insertable lighting device 1 includes a retainer 30 attached to the exterior surface 61 of pliable sheath 16, in which retainer 30 is positioned between ring stop 28 and second optical fiber assembly end 46, in which case the method of the present invention, with some embodiments, further includes attaching retainer 30 to an external support 109. For purposes of non-limiting illustration, external support 109 includes a base 112, an upward extending rod 115, and a laterally extending rod 118 that is attached to retainer 30. With some embodiments, the retainer 30 is attached to an external support (such as external support 109) after the incision blade 12 and insertable sheath 10 have been withdrawn from the internal cavity 97.

The light source assembly (such as light source assembly 22) of the insertable lighting device of the present invention further includes a power source (such as power source 24) and a power adjuster (such as power adjuster 26), as described previously herein, in which case the method of the present invention further includes, with some embodiments, adjusting the power adjuster thereby adjusting an amount of illumination within the internal cavity. The power adjuster, with some embodiments, is adjusted manually.

The direction that the first optical fiber assembly end 43 faces can be adjusted, with some embodiments, by one or more separate devices (not shown), such as one or more clamps, that are separately inserted into internal cavity 97. A portion of the optical fiber assembly 40 can be gripped and bent by one or more clamps (not shown) within internal cavity 97, which results in the first optical fiber assembly end 43 facing a desired direction and correspondingly illuminating a desired portion or portions of internal cavity 97.

The insertable lighting device, with some embodiments of the present invention, is an insertable internal cavity surgical lighting device, and the internal cavity into which it is inserted in accordance with the method of the present invention, is an internal animal cavity. The insertable lighting device, with some embodiments, is used in conjunction with procedures (such as diagnostic and/or surgical procedures) performed on/in vertebrates, such as fish, amphibians, reptiles, birds, and mammals, and correspondingly the internal animal cavity is an internal fish cavity, an internal amphibian cavity, an internal reptile cavity, an internal bird cavity, or an internal mammal cavity. In accordance with some further embodiments, the insertable lighting device of the present invention is used in conjunction with procedures (such as diagnostic and/or surgical procedures) performed on/in humans, and the internal animal cavity is an internal human cavity, such as, but not limited to, an internal human abdominal cavity.

The present invention has been described with reference to specific details of particular embodiments thereof. It is not intended that such details be regarded as limitations upon the scope of the invention except insofar as and to the extent that they are included in the accompanying claims.

What is claimed is:

1. An insertable lighting device comprising:
   (a) an optical fiber assembly comprising,
      (i) an optical fiber that is encased at least partially within
      (ii) a pliable sheath,
      wherein said optical fiber assembly is flexible, and has a first optical fiber assembly end that is adapted to emit light, a second optical fiber assembly end, and a first length, said first optical fiber assembly end facing a forward direction;
   (b) an introducer sheath having a second length that is less than said first length and comprising,
      (i) a first introducer sheath end that comprises an incision blade,
      (ii) a second introducer sheath end, and
      (iii) an elongated interior cavity,
      wherein said optical fiber assembly resides slidably within said elongated interior cavity of said introducer sheath,
      said introducer sheath is slidably positionable over and along said optical fiber assembly, and
      said first introducer sheath end faces said forward direction; and
   (c) a light source assembly attached to said second optical fiber assembly end, said light source assembly comprising a light source that introduces light into said optical fiber,
   wherein said second introducer sheath end comprises a ring extending outwardly from an exterior surface of said introducer sheath, and
   said insertable lighting device further comprises,
   a ring stop extending outwardly from an exterior surface of said pliable sheath, said ring stop being positioned between said second optical fiber assembly end and said second introducer sheath end,
      wherein said ring stop and said ring of said introducer sheath are each dimensioned to engage snap-fittingly with each other.

2. The insertable lighting device of claim 1, wherein at least a portion of an exterior surface of said introducer sheath is defined by a plurality of ribs.

3. The insertable lighting device of claim 1, wherein said light source assembly further comprises,
   a power source, and
   a power adjuster.

4. The insertable lighting device of claim 3, wherein said power source comprises at least one battery.

5. The insertable lighting device of claim 1, wherein the light, introduced into said optical fiber by said light source, is selected from visible light, infrared light, ultraviolet light, and combinations thereof.

6. The insertable lighting device of claim 5, wherein the light, introduced into said optical fiber by said light source, comprises substantially coherent light.

7. The insertable lighting device of claim 1 further comprising,
   a retainer attached to an exterior surface of said pliable sheath, said retainer being positioned between said second introducer sheath end and said second optical fiber assembly end.

8. The insertable lighting device of claim 7, wherein said retainer extends substantially laterally outward from said optical fiber assembly.

9. The insertable lighting device of claim 7, wherein said retainer is a retainer clip.

10. The insertable lighting device of claim 1 further comprising,
    a retainer attached to said exterior surface of said pliable sheath, wherein said retainer is positioned between said ring stop and said second optical fiber assembly end.

11. The insertable lighting device of claim 1, wherein said first optical fiber assembly end is dimensioned to be withdrawn within said elongated interior cavity of said introducer sheath.

12. The insertable lighting device of claim 1, wherein said insertable lighting device is an insertable internal cavity surgical lighting device.

13. A method of illuminating an internal cavity comprising:
    (A) providing an insertable lighting device comprising,
       (a) an optical fiber assembly comprising,
          (i) an optical fiber that is encased at least partially within
          (ii) a pliable sheath,
          wherein said optical fiber assembly is flexible, and has a first optical fiber assembly end that is adapted to emit light, a second optical fiber assembly end, and a first length, said first optical fiber assembly end facing a forward direction,
       (b) an introducer sheath having a second length that is less than said first length and comprising,
          (i) a first introducer sheath end that comprises an incision blade,
          (ii) a second introducer sheath end, and
          (iii) an elongated interior cavity,
          wherein said optical fiber assembly resides slidably within said elongated interior cavity of said introducer sheath,
          said introducer sheath is slidably positionable over and along said optical fiber assembly, and
          said first introducer sheath end faces said forward direction, and
       (c) a light source assembly attached to said second optical fiber assembly end, said light source assembly comprising a light source that introduces light into said optical fiber;
    (B) positioning at least one of, (i) said introducer sheath, and (ii) said optical fiber assembly, such that, said incision blade of said introducer sheath is positioned forward of said first optical fiber assembly end;
    (C) inserting said incision blade and a portion of said introducer sheath through a cavity wall into said internal cavity;
    (D) positioning at least one of, (i) said introducer sheath, and (ii) said optical fiber assembly, such that said first optical fiber assembly end is positioned forward beyond said incision blade and within said internal cavity;
    (E) illuminating at least a portion of said internal cavity with light emanating from said first optical fiber assembly end;
    (F) withdrawing said incision blade and said introducer sheath from said internal cavity, such that said incision blade is positioned externally of an outer surface of said cavity wall, and said first optical fiber assembly end is positioned within said internal cavity, wherein said second introducer sheath end comprises a ring extending outwardly from an exterior surface of said introducer sheath, and said insertable lighting device further comprises, a ring stop extending outwardly from an exterior surface of said pliable sheath, said ring stop being positioned between said second optical fiber assembly end and said second introducer sheath end, wherein said ring stop and said ring of said introducer sheath are each dimensioned to engage abuttingly with each other, and said method further comprising, after withdrawing said incision blade and said introducer sheath from said internal cavity, (G) positioning abuttingly together said ring of said introducer sheath and said ring stop, wherein said ring of said introducer sheath and said ring stop are each adapted to engage snap-fittingly with each other, and said ring of said introducer sheath and said ring stop engage snap-fittingly with each other.

14. The method of claim 13 wherein, said insertable lighting device further comprises, a retainer attached to said exterior surface of said pliable sheath, wherein said retainer is positioned between said ring stop and said second optical fiber assembly end, said method further comprising, attaching said retainer to an external support.

15. The method of claim 13 wherein, said light source assembly further comprises, a power source, and a power adjuster, and said method further comprises adjusting said power adjuster thereby adjusting an amount of illumination within said internal cavity.

16. The method of claim 13, wherein said insertable lighting device is an insertable internal cavity surgical lighting device, and said internal cavity is an internal animal cavity.

* * * * *

UNITED STATES PATENT AND TRADEMARK OFFICE
CERTIFICATE OF CORRECTION

| | | |
|---|---|---|
| PATENT NO. | : 9,517,003 B2 | Page 1 of 1 |
| APPLICATION NO. | : 14/287306 | |
| DATED | : December 13, 2016 | |
| INVENTOR(S) | : Meng-G Martin Lee | |

It is certified that error appears in the above-identified patent and that said Letters Patent is hereby corrected as shown below:

In the Specification

Column 1, Line 7, delete "61/856,328,filed" and insert -- 61/856,328, filed --

Column 1, Line 7, delete "2013,the" and insert -- 2013, the --

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*